(12) United States Patent
Morishita et al.

(10) Patent No.: US 8,277,755 B2
(45) Date of Patent: Oct. 2, 2012

(54) APPARATUS FOR DISCHARGING PACKING MATERIAL FROM SAMPLE COLUMN

(75) Inventors: Keisuke Morishita, Hiratsuka (JP); Takayuki Okafuji, Chigasaki (JP); Shuichi Akasaka, Chigasaki (JP)

(73) Assignee: Mitsubishi Chemical Analytech Co., Ltd., Yokkaichi-shi, Mie-Ken (JP)

( * ) Notice: Subject to any disclaimer, the term of this patent is extended or adjusted under 35 U.S.C. 154(b) by 104 days.

(21) Appl. No.: 12/993,008

(22) PCT Filed: May 23, 2008

(86) PCT No.: PCT/JP2008/001293
§ 371 (c)(1),
(2), (4) Date: Jan. 13, 2011

(87) PCT Pub. No.: WO2009/141854
PCT Pub. Date: Nov. 26, 2009

(65) Prior Publication Data
US 2011/0147418 A1    Jun. 23, 2011

(51) Int. Cl.
*B67D 7/06* (2010.01)
(52) U.S. Cl. ..... 422/500; 422/243; 422/522; 435/286.2; 436/161; 366/108; 210/109; 210/198.2; 210/225
(58) Field of Classification Search ............ 422/500, 422/243, 522; 435/286.2; 436/161; 210/198.2; 210/225; 366/108
See application file for complete search history.

(56) References Cited

U.S. PATENT DOCUMENTS 5,167,809 A * 12/1992 Mann et al. ............ 210/198.2
5,282,973 A * 2/1994 Mann ...................... 210/656

(Continued)

FOREIGN PATENT DOCUMENTS
EP    0 476 998 A2    3/1992
(Continued)

OTHER PUBLICATIONS

Supplementary European Search Report in EP 08 75 1802 dated Nov. 10, 2011.

(Continued)

*Primary Examiner* — In Suk Bullock
*Assistant Examiner* — Timothy G Kingan
(74) *Attorney, Agent, or Firm* — Nixon & Vanderhye P.C.

(57) ABSTRACT

The present invention provides an apparatus for discharging packing material from a sample column which is capable of removing the packing material such as activated carbon from the sample column for analysis having a tube shape smoothly and more certainly, and can be suitably used in the case where the packing material thus removed is supplied to an analyzer, etc. The apparatus for discharging packing material according to the present invention comprises a discharge apparatus body (4) which is disposed concentrically to the sample column (9) held in a predetermined position, and is capable of moving close to and away from the sample column; a column positioning hub (5) which is mounted to a tip end of the discharge apparatus body to be movable forward and rearward, and biased toward the sample column (9); a push-out pin which is inserted into the discharge apparatus body (4) and the column positioning hub (5) to extend substantially along center lines of the discharge apparatus body and the column positioning hub, and allowed to relatively project from the column positioning hub when the column positioning hub (5) is moved rearward; and a vibration generating means for applying vibration to the push-out pin (6) when the push-out pin is allowed project from the column positioning hub.

3 Claims, 3 Drawing Sheets

U.S. PATENT DOCUMENTS

| | | | |
|---|---|---|---|
| 5,366,621 A * | 11/1994 | Bidell et al. | 210/198.2 |
| 5,585,068 A | 12/1996 | Panetz et al. | |
| 5,667,675 A * | 9/1997 | Hatch et al. | 210/198.2 |
| 6,001,260 A * | 12/1999 | Hatch et al. | 210/656 |
| 6,036,855 A * | 3/2000 | Shalon et al. | 210/198.2 |
| 7,169,307 B2 * | 1/2007 | Liu | 210/635 |
| 7,718,058 B2 * | 5/2010 | Agee et al. | 210/198.2 |
| 2003/0146159 A1 | 8/2003 | Guiochon | |
| 2005/0224414 A1 * | 10/2005 | Izzo et al. | 210/656 |

FOREIGN PATENT DOCUMENTS

| | | |
|---|---|---|
| JP | 52-117878 | 10/1977 |
| JP | 58-132662 | 8/1983 |
| JP | 62-297753 | 12/1987 |
| JP | 63-103967 | 5/1988 |
| JP | 2001-269565 | 10/2001 |
| JP | 2004-233335 | 8/2004 |
| JP | 2004-526134 | 8/2004 |

OTHER PUBLICATIONS

International Search Report for PCT/JP2008/001293, mailed Jun. 17, 2008.

* cited by examiner

APPARATUS FOR DISCHARGING PACKING MATERIAL FROM SAMPLE COLUMN

This application is the U.S. national phase of International Application No. PCT/JP2008/001293, filed 23 May 2008, which designated the U.S., the entire contents of which is hereby incorporated by reference.

TECHNICAL FIELD

The present invention relates to an apparatus for discharging packing material from a sample column, and more particularly, to an apparatus for discharging packing material which is adapted to remove the packing material such as activated carbon filled in a sample column for analysis having a tube shape and supplying the thus removed packing material to an analyzer.

BACKGROUND ART

For example, upon analysis of total organic halogens contained in environmental waters such as river or lake water or in various industrial waste waters, by using an adsorption apparatus for the total organic halogens, a liquid sample is flowed through a sample column of a tube shape filled with activated carbon to adsorb the total organic halogen compounds contained in the liquid sample onto the activated carbon, and then the thus obtained organic halogen compounds are analyzed by an analyzer for organic halogens. In such an analysis, the activated carbon filled in the sample column is discharged and received in a reaction tube, and the reaction tube is heated to convert the total organic halogen compounds in the sample into hydrogen halides, followed by measuring concentrations of the total organic halogens by an potentiometric titration method.

Non-Patent Document 1: Dia Instruments, Co., Ltd., "Method for Measuring Chlorine"; [Online]; Searched on Oct. 27, 2006; Internet URL:

<http://www.dins.co.jp/dins_j/3seihin/genri/gts300cl.htm>,
<http://www.dins.co.jp/dins_j/3seihin/kklabop/aqf100option.htm#asc120s>

DISCLOSURE OF THE INVENTION

Problems to be Solved by the Invention

Incidentally, in the above analyzing procedure, in order to efficiently perform the analyzing work, it is desirable to not only use an analyzer equipped with a reaction tube having a vertical structure, but also utilize a so-called auto-sample changer (automatic sample supply device) in which when discharging the activated carbon from the sample column and inserting the activated carbon into the reaction tube of the analyzer, a plurality of the sample columns are successively supplied to a sample feed inlet of the reaction tube by means of a turn table such that the activated carbon filled in each sample column is sequentially pushed down into the reaction tube by up and down motion of a push-out pin.

However, the above sample column is in the form of a capillary tube which is formed of a quartz glass and has an inner diameter of about 3 mm, and the activated carbon filled in the sample column is sealed at both ends thereof with an alumina fiber, etc. Therefore, in the case where the sample such as water is adsorbed onto the activated carbon, there tends to occur such a condition that the activated carbon and the alumina fiber are firmly attached to the inner wall of the sample column owing to the water adsorbed thereto. For this reason, when using the above auto-sample changer, the alumina fiber and the activated carbon tend to be entangled and stuck around the push-out pin, so that there tends to arise such a problem that smooth discharge of the sample from each sample column into the reaction tube of the analyzer is hardly accomplished even by the up and down motion of the push-out pin.

The present invention has been completed to solve the above conventional problems. An object of the present invention is to provide an apparatus for discharging packing material from a sample column for analysis which can be suitably used in the case where the packing material such as activated carbon which is filled in the sample column is discharged therefrom and supplied to an analyzer, and which is capable of discharging the packing material from the sample column for analysis smoothly and more certainly.

Means for Solving Problems

In order to solve the above conventional problems, in accordance with the present invention, there is provided an apparatus for discharging packing material from a sample column which is adapted to remove the packing material filled in the sample column having a tube shape, comprising:

a tubular discharge apparatus body which is disposed concentrically to the sample column held in a predetermined position by means of a holding mechanism for the sample column, and which is capable of moving close to and away from the sample column;

a column positioning hub which is mounted to a tip end of the discharge apparatus body on its side facing to the sample column so as to be movable forward and rearward, and which is biased toward the sample column;

a push-out pin which is inserted into the discharge apparatus body and the column positioning hub to extend substantially along center lines of the discharge apparatus body and the column positioning hub, and which is allowed to relatively project from a tip end of the column positioning hub when the column positioning hub is moved rearward; and a vibration generating means for applying vibration to the push-out pin when the push-out pin is allowed to project from the column positioning hub.

That is, in the above apparatus for discharging packing material, the discharge apparatus body is allowed to move close to the tube-shaped sample column held in a predetermined position to press the column positioning hub disposed on the side of the tip end of the discharge apparatus body against the tip end of the sample column, so that the sample column is accurately positioned. In addition, when the column positioning hub is relatively moved rearward by pressing the column positioning hub against the sample column, the push-out pin inserted into the discharge apparatus body and the column positioning hub is allowed to project therefrom, and inserted into the sample column to thereby push the packing material out of the sample column. When pushing out the packing material, the push-out pin is brought into contact with the packing material while being vibrated to thereby apply vibration to the packing material. As a result, adhesion of the packing material to the inner wall of the sample column can be reduced, and the packing material can be prevented from being entangled and stuck around the push-out pin.

Effect of the Invention

In the apparatus for discharge packing material according to the present invention, the packing material is pushed out from the sample column by the push-out pin while vibrating the push-out pin, so that adhesion of the packing material to the inner wall of the sample column can be reduced, and the packing material can be prevented from being entangled and stuck around the push-out pin. As a result, it is possible to discharge the packing material from the sample column smoothly and more certainly.

EXPLANATION OF REFERENCE NUMERALS

10: Pedestal; 11: Support plate; 20: Motor; 21: Pulley; 22: Timing belt; 23: Pulley; 30: Guide rod; 31: Lifting plate; 34: Mount base for discharge apparatus body; 4: Discharge apparatus body; 5: Column positioning hub; 51: Throttled portion; 52: Column engaging hole; 6: Push-out pin; 62: Spring; 7: Motor (as vibration generating means); 70: Rotation axis; 71: Eccentric joint (as vibration generating means); 81: Turn table (as sample column holding mechanism); 82: Sample feed inlet; 9: Sample column

PREFERRED EMBODIMENTS FOR CARRYING OUT THE INVENTION

Figure 1:
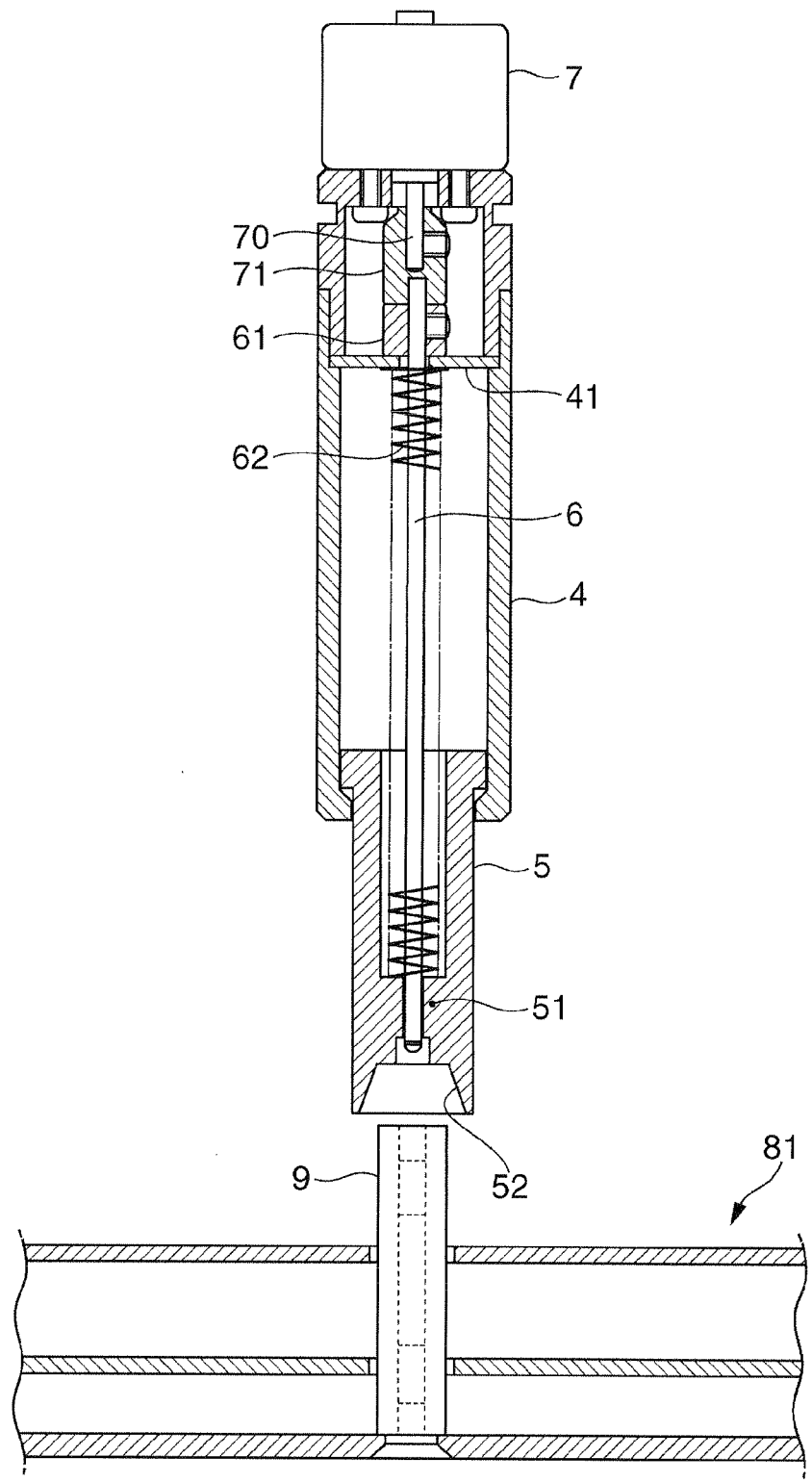
FIG. 1 is a vertical sectional view showing a structure of a main part of an apparatus for discharging packing material according to the present invention.
Figure 2:
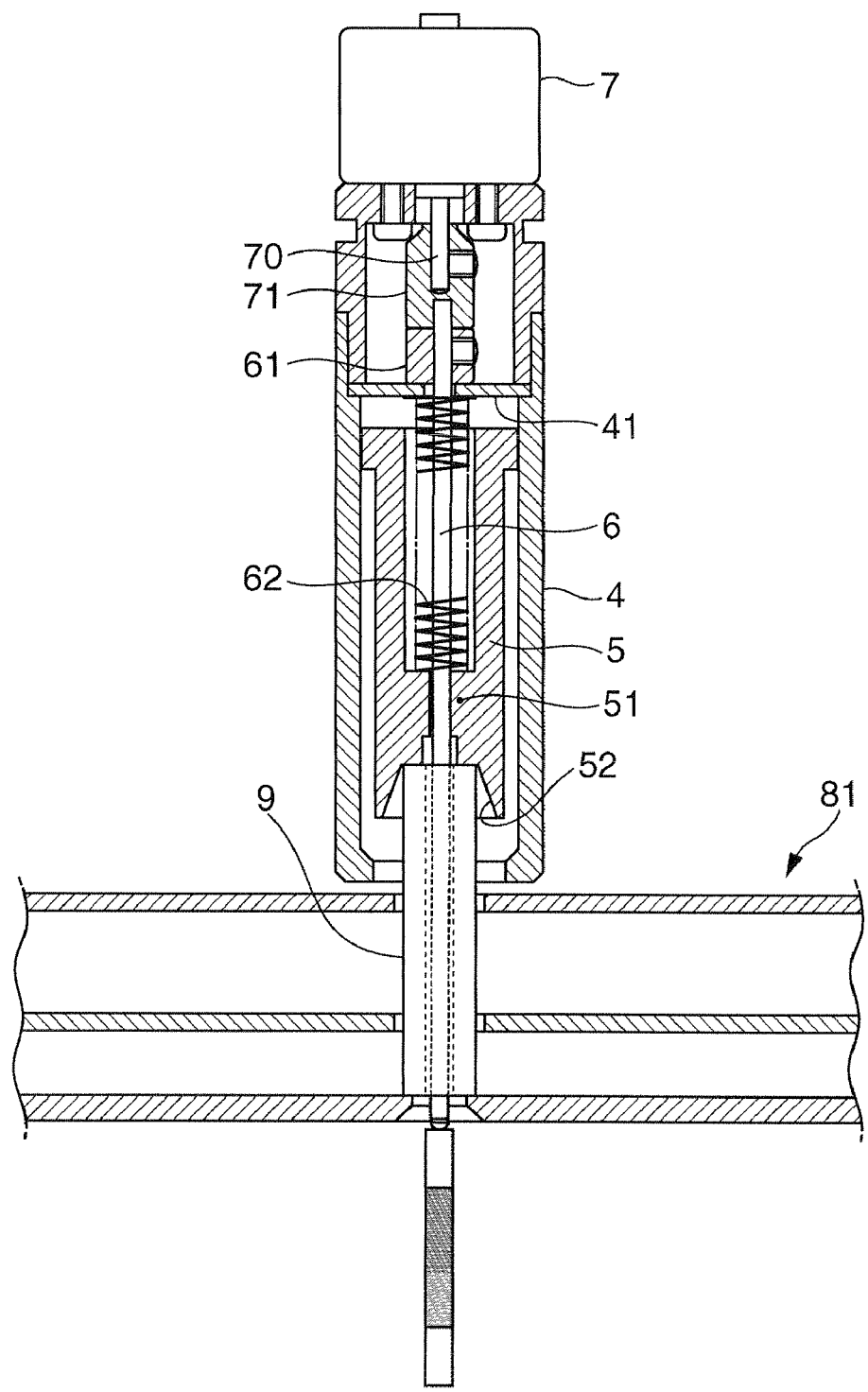
FIG. 2 is a vertical sectional view showing the structure of the main part of the apparatus for discharging packing material according to the present invention as shown in FIG. 1 when the apparatus is operated.
Figure 3:
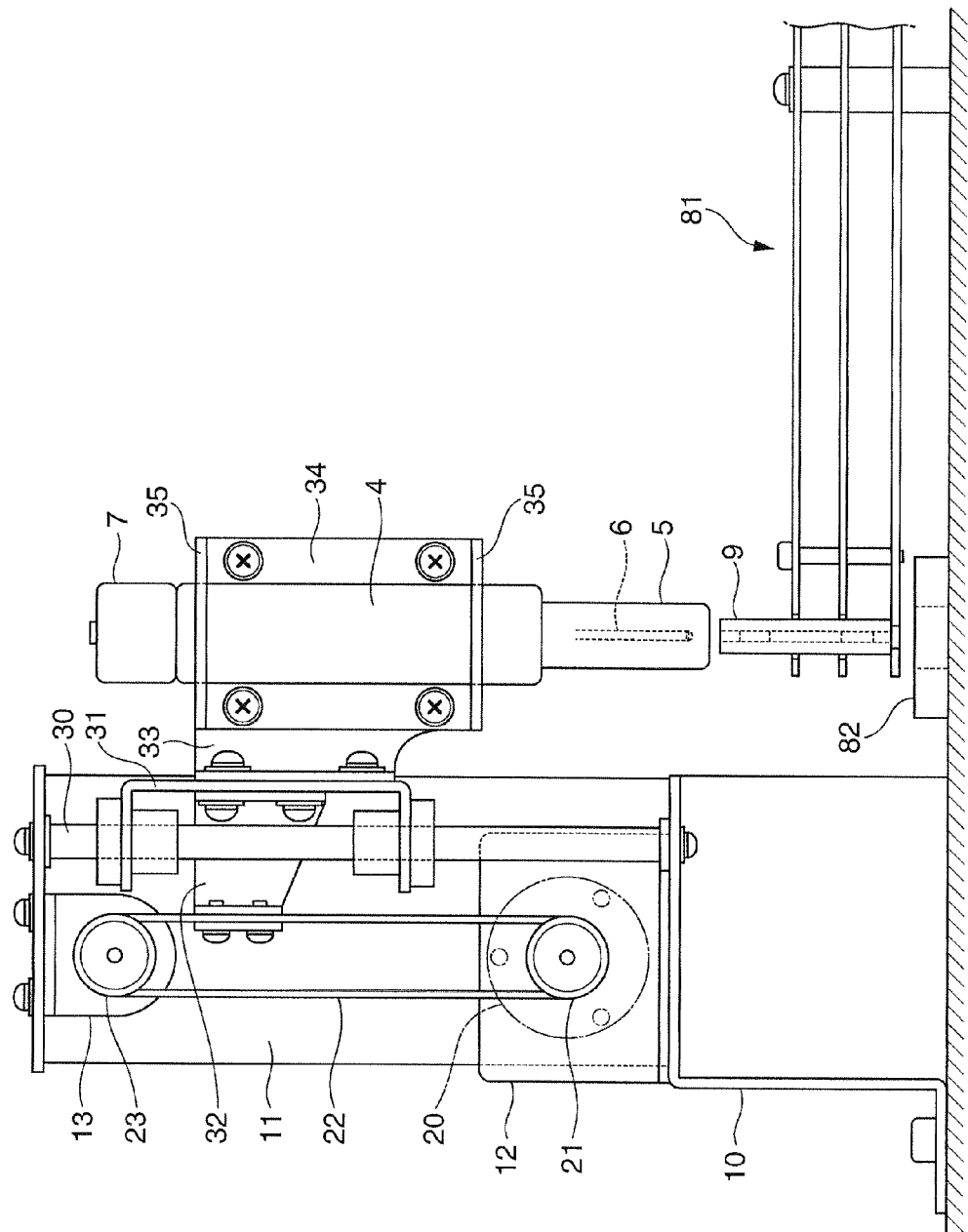
FIG. 3 is a side view showing a whole structure of the apparatus for discharging packing material according to the present invention.

An embodiment of the apparatus for discharging packing material from a sample column according to the present invention is explained below by referring to the accompanying drawings. FIG. 1 is a vertical sectional view showing a structure of a main part of the apparatus for discharging packing material according to the present invention. FIG. 2 is a vertical sectional view showing the structure of the main part of the apparatus for discharging packing material according to the present invention as shown in FIG. 1 when the apparatus is operated. FIG. 3 is a side view showing a whole structure of the apparatus for discharging packing material according to the present invention.

As shown in FIG. 3, the apparatus for discharging packing material according to the present invention is used for removing the packing material filled in a tube-shaped sample column (9) and supplying the thus removed packing material, for example, to an analyzer. Examples of the analyzer include an organic halogen analyzer which comprises a vertical reaction tube provided at an upper end thereof with a sample feed inlet (82; refer to FIG. 3) and serves for measuring concentrations of total organic halogen compounds contained in water. The sample column (9) used for analysis of the total organic halogens, etc., is in the form of a tube having an outer diameter of about 13 mm, an inner diameter of about 3 mm and a length of about 50 mm which is formed of a quartz glass. The tube-shaped sample column is filled with activated carbon and sealed at both ends thereof with an alumina fiber.

In the above analysis for the total organic halogens, a liquid sample is flowed through the sample column (9) filled with the activated carbon to adsorb the total organic halogen compounds in the liquid sample into the activated carbon. Thereafter, the activated carbon and the alumina fiber as packing materials in the sample column (9) is discharged and received in a reaction tube (not shown) of the analyzer, and then the reaction tube is heated to convert the total organic halogen compounds in the liquid sample into hydrogen halides. The resulting reaction solution is subjected to potentiometric titration to measure concentrations of the total organic halogens. In the above analysis, a plurality of the sample columns (9) are successively delivered to the position in the close vicinity of a sample feed inlet (82) of the reaction tube of the analyzer by means of a turn table (81) (only partially shown in the drawings) as a sample column holding mechanism (only one sample column is shown in FIG. 3). The apparatus for discharging packing material according to the present invention is applied to both removal of a packing material (such as activated carbon and alumina fiber) from the sample column (9) and insertion of the packing material into the sample feed inlet (82) of the reaction tube.

Meanwhile, the turn table (81) has such a structure that two circular ring-shaped guide tables are concentrically stacked above a disk-shaped support table at equal vertical intervals, for example, spaced apart by a distance corresponding to about ¼ to about ⅓ time a height of the sample column from each other. A number of sample dropping holes each having a diameter which is smaller than the outer diameter of the sample column (9) but larger than the inner diameter of the sample column (9) are provided at constant pitches along the outer circumferential periphery of the support table. Whereas, each of the guide tables is provided with column holding holes into which the respective sample columns are loosely engaged, at the positions respectively aligned with the sample dropping holes. The turn table (81) is so arranged as to intermittently rotate at constant angular intervals in synchronous relation to operation of the apparatus for discharging packing material such that the respective sample dropping holes are sequentially positioned just above the sample feed inlet (82).

As shown in FIG. 3, the apparatus for discharging packing material according to the present invention comprises a tubular discharge apparatus body (4) disposed concentrically to the sample column (9) which is held at a predetermined position, i.e., at the position close to the sample feed inlet (82) when applied to the above analyzer, by means of the turn table (81) as a sample column holding mechanism, so as to move close to and away from the sample column; a column positioning hub (5) which is mounted to a tip end of the discharge apparatus body (4) on the side facing to the sample column so as to be movable forward and rearward, and which is biased toward the sample column (9); and a push-out pin (6) which is inserted into the discharge apparatus body (4) and the column positioning hub (5) to extend substantially along central lines of the discharge apparatus body (4) and the column positioning hub (5), and which is allowed to relatively project from a tip end of the column positioning hub (5) when the column positioning hub (5) is moved rearward and retracted into the apparatus body (4).

For example, in the case where the reaction tube of the analyzer is disposed in the vertical direction, the apparatus for discharging packing material according to the present invention is installed above a casing of the analyzer similarly to the turn table (81). The discharge apparatus body (4) is lifted or lowered relative to the sample column (9) vertically held by the turn table (81) so as to move close to and away from the sample column (9). As an elevating mechanism for lifting and lowering the discharge apparatus body (4), there may be used such a belt-driven device as shown in FIG. 3.

More specifically, the elevating mechanism is constructed on a pedestal (10) which is mounted on an upper portion of the casing of the analyzer and designed to have a height larger to some extent than that of the turn table (81). On an upper surface of the pedestal (10), a motor (20) such as a DC servo motor is mounted through a motor mounting plate (12) disposed in an approximately vertical direction. A pulley (21) is fitted to a rotation axis of the motor (20) which is projected horizontally. In addition, on the back side of the motor (20) opposed to the pulley (21), a support plate (11) provided at an upper end thereof with an overhang plate is vertically disposed. On a lower surface side of the overhang plate, a pulley (23) is mounted thereto through a pulley mounting plate (13) at the position corresponding to the pulley (21). A timing belt (22) is wound around the pulley (21) and the pulley (23), and reciprocatively rotated in an up and down direction according to forward or reverse rotation of the motor (20).

On an upper surface of the pedestal (10) on a side of the timing belt (22), a guide rod (30) is vertically disposed to extend from the pedestal toward the overhung plate of the support plate (11). A lifting plate (31) having a generally U-shaped vertical section is slidably mounted to the guide rod (30) through two bearings respectively provided at upper and lower side portions thereof. On a side surface of the lifting plate (31) on the side opposed to the timing belt (22), a flat mount base (34) for the discharge apparatus body is uprightly mounted to the lifting plate through a plate-shaped base mounting bracket perpendicularly overhung from the side surface of the lifting plate in an folding screen manner. On the other hand, on a side surface of the lifting plate (31) on the side facing to the timing belt (22), a plate-shaped belt latch fitting (32) is perpendicularly overhung therefrom in an folding screen manner. The belt latch fitting (32) is fixedly coupled at its tip end to the timing belt (22).

The mount base (34) for the discharge apparatus body serves as a metal member for vertically supporting the discharge apparatus body (4). The discharge apparatus body (4) is mounted to the mount base (34) for the discharge apparatus body through metal fixtures (35), (35) which are respectively engaged with upper and lower end peripheral portions of the mount base (34). More specifically, the discharge apparatus body (4) is reciprocally elevated and lowered within a predetermined range in the vertical direction according to the forward and reverse rotation of the motor (20). Meanwhile, although not shown in the drawings, a position detecting sensor for detecting an end of the moving timing belt (22) and controlling rotation of the motor (20) is provided on the side of the timing belt (22). The motion of the discharge apparatus body (4) is controlled by the motor (20) to limit an advancing end (lowering end) and a retracting end (lifting end) thereof.

The discharge apparatus body (4) is formed, for example, into an inverted closed-bottom cylindrical shape as shown in FIG. 1, and is mounted to the mount base (34) for the discharge apparatus body in the elevating mechanism and thereby positioned vertically just above the sample feed inlet (82). The tip end (lower end) of the discharge apparatus body (4) is formed into an open end whose diameter is slightly smaller than an inner diameter of the discharge apparatus body. The discharge apparatus body (4) accommodates the below-mentioned spring (62) therein, and the inside of the discharge apparatus body (4) is divided into two chambers by a partition (41) disposed at an upper portion thereof to urge the spring downward.

The column positioning hub (5) is formed into a generally cylindrical shape which is provided at a lower portion thereof with a throttled portion (51) whose inner diameter is reduced. An outer diameter portion of the column positioning hub (5) except for its rear end (upper end) portion has such a diameter as received in the tip end opening (lower end opening) of the discharge apparatus body (4), and the rear end (upper end) portion of the column positioning hub (5) has an increased diameter capable of engaging in an inner diameter portion of the discharge apparatus body (4). More specifically, the column positioning hub (5) is accommodated in the discharge apparatus body (4) so as not to fall out of the tip end opening but so as to project therefrom and retract thereinto. Meanwhile, the throttled portion (51) of the column positioning hub (5) is configured to allow the push-out pin (6) to loosely engage therein, and has a function of restricting a floating motion of the push-out pin (6).

The column positioning hub (5) is biased toward the side of the sample column (9) held on the turn table (81). More specifically, the spring (62) in the form of a compression coil spring is accommodated within the discharge apparatus body (4). The rear end (upper end) of the spring (62) is brought into abutting contact with the partition (41) of the discharge apparatus body (4), whereas the tip end (lower end) of the spring (62) is brought into abutting contact with the throttled portion (51) in the column positioning hub (5). With such a construction, the column positioning hub (5) is always biased toward the side of the sample column (9) and held to project from the tip end of the discharge apparatus body (4).

The push-out pin (6) is inserted into the discharge apparatus body (4) and the column positioning hub (5) as well as the spring (62) to extend substantially along center lines of the discharge apparatus body (4) and the column positioning hub (5). The rear end portion (upper end portion) of the push-out pin (6) is penetrated through the partition (41) in the discharge apparatus body (4), and coupled to a push-out pin supporting collar (61) disposed in a rear end side space (upper space) within the discharge apparatus body (4) so as not to fall downwardly therefrom. On the other hand, the tip end portion (lower end portion) of the push-out pin (6) extends up to the throttled portion (51) of the column positioning hub (5) when the apparatus is kept in a stand-by condition. With this arrangement, as shown in FIG. 2, when the column positioning hub (5) is retracted into an inside of the discharge apparatus body (4), the push-out pin (6) is allowed to relatively project toward the side of the tip end of the column positioning hub (5). Meanwhile, the tip end (lower end) of the push-out pin (6) is chamfered to prevent the tip end of the sample column (9) from being damaged by the contact therewith when the push-out pin is inserted into the sample column (9).

In addition, the column positioning hub (5) has a positioning structure for accurately positioning the sample column (9) concentrically thereto, for example, when treating the sample column (9) delivered by the turn table (81). More specifically, as shown in FIG. 1, the column positioning hub (5) is provided at a tip end portion (lower end portion) thereof with a column engaging hole (52) of a truncated cone shape which is engaged with the tip end (upper end) of the sample column (9) and has a diameter gradually reduced toward the rear end (upper end) of the column positioning hub.

That is, as shown in FIG. 2, the column positioning hub (5) has such an automatic aligning function that when the tip end (lower end) of the column positioning hub (5) comes into abutting contact with the sample column (9), the tip end (upper end) of the sample column is allowed to relatively advance into the column engaging hole (52) so as to position the sample column (9) concentrically to the center line of the column positioning hub. With this arrangement, the push-out pin (6) can be more certainly inserted into the sample column (9) without damage to the sample column (9).

The apparatus for discharging packing material according to the present invention is further provided with a vibration generating means for applying vibration to the push-out pin (6) when the push-out pin (6) is allowed to project from the column positioning hub (5) in order to reduce adhesion of the packing material to the inner wall of the sample column (9) and prevent the packing material from being entangled and stuck around the push-out pin (6). In the present invention, by vibrating the push-out pin (6), it is possible to certainly remove the packing material from the sample column (9).

As the above vibration generating means, there may be used various types of small vibrators. For example, as shown in FIG. 1, the vibration generating means comprises a motor (7) disposed at a rear end portion (upper end portion) of the discharge apparatus body (4) and an eccentric joint (71) for connecting a rotation axis (70) of the motor with the rear end (upper end) of the push-out pin (6) in an eccentric condition. As the motor (7), there may be usually used a DC motor usually having a rotation speed of about 2000 to about 4000 rpm.

The eccentric joint (71) is constructed from a generally cylindrical block, and is provided at a center of a rear end surface (upper end surface) thereof with a rotation axis insert hole into which the rotation axis (70) of the motor (7) is inserted. The eccentric joint (71) is fixedly coupled to the rotation axis (70) of the motor (7) which is inserted into the rotation axis insert hole, by means of a set screw. In addition, the eccentric joint (71) is provided at a position offset from a center of the tip end surface (lower end surface) thereof with a push-out pin insert hole into which the rear end portion (upper end portion) of the push-out pin (6) projecting upwardly beyond the push-out pin supporting collar (61) is inserted. The push-out pin (6) is slidably inserted into the push-out pin insert hole.

The amount of offset between the rotation axis inert hole and the push-out pin insert hole in the eccentric joint (71) is adjusted to about 0.4 to about 1.2 mm. In other words, the push-out pin (6) is eccentrically disposed with the above offset amount relative to the rotation axis (70) of the motor (7). Therefore, the push-out pin (6) undergoes fine rotation at a high speed so as to draw a circle having a radius of about 0.4 to about 1.2 mm around the rotation axis of the motor (7) in association with rotation of the motor when viewed in plane from the side of the rear end (upper end) of the push-out pin (6).

On the other hand, as shown in FIG. 2, when the column positioning hub (5) is retracted to allow the push-out pin (6) to project therefrom, the apparatus is configured such that deflection of an approximately central portion of the push-out pin (6) is limited by the throttled portion (51) of the column positioning hub (5). With this arrangement, when operating the motor (7), the tip end (lower end) of the push-out pin (6) undergoes fine rotation at a high speed around the throttled portion (61) as a rotation center in an approximately symmetrical relation to the rear end (upper end) of the push-out pin (6). As a result, the push-out pin (6) is brought into vibrated condition. Meanwhile, the motor (7) starts to rotate when initiation of advancing (lowering) of the discharge apparatus body (4) is detected by the detecting sensor for detecting the end of the moving timing belt (22). Whereas, the rotation of the motor (7) is stopped when the discharge apparatus body (4) reaches its advancing end (lowering end).

The apparatus for discharging packing material according to the present invention is operated as follows upon the treatment for removing the packing material from the sample column (9). For example, in the above analysis of total organic halogens, as shown in FIG. 3, the sample column (9) is delivered just above the sample feed inlet (82) of the reaction tube of the analyzer by rotation of the turn table (81). At the time at which the sample column (9) is held in the predetermined position, the motor (20) in the apparatus for discharging packing material is actuated.

In the apparatus for discharging packing material, when the timing belt is travelled by rotation of the motor (20), the discharge apparatus body (4) mounted to the mount base (34) for the discharge apparatus body is advanced (lowered), whereby the discharge apparatus body (4) is allowed to move close to the sample column (9) so that the column positioning hub (5) disposed on the tip end side of the discharge apparatus body is pressed against the tip end (upper end) of the sample column (9). Thereupon, since the column positioning hub (5) is provided at its tip end with the engaging hole (52) whose diameter is gradually reduced toward the rear end side thereof, the sample column (9) loosely engaged in the column holding hole of the turn table (81) can be certainly positioned concentrically to the column positioning hub (5) by pressing the tip end of the column positioning hub (5) against the sample column (9).

Next, as shown in FIG. 2, when the tip end (lower end) of the discharge apparatus body (4) is further advanced (lowered) to the position close to an upper surface of the turn table (81), the motor (20) is stopped to rotate. In this case, when the discharge apparatus body (4) is advanced (lowered) from the position at which the tip end (upper end) of the sample column (9) is brought into contact with the engaging hole (52) provided at the tip end of the column positioning hub (5) to the position at which the tip end of the discharge apparatus body (4) is located in the close vicinity of the turn table (81), the column positioning hub (5) is relatively retracted into the discharge apparatus body (4) by pressing it against the sample column (9). As a result, with the retraction of the column positing hub (5), the push-out pin (6) is allowed to project from the tip end of the column positioning hub (5), and advanced into an inside of the sample column (9) to push out the packing material filled therein (such as activated carbon and alumina fiber) therefrom.

In the present invention, when the above packing material is pushed out, in other words, when the push-out pin (6) is allowed to project from the column positioning hub (5) and advanced into the sample column (9), the motor (7) as a vibration generating means is rotated to apply vibration to the push-out pin (6). That is, the rotation axis (70) of the motor (7) installed in the discharge apparatus body (4) is coupled with the push-out pin (6) through the eccentric joint (71), so that the rear end (upper end) of the push-out pin (6) is allowed to undergo fine rotation at a high speed. As a result, the tip end (lower end) of the push-out pin (6) is also allowed to undergo fine rotation at a high speed in an approximately symmetrical relation to the rear end thereof around the throttled portion (51) of the column positioning hub (5) as a rotation center, thereby causing the tip end of the push-out pin (6) to vibrate.

As described above, in the apparatus for discharging packing material according to the present invention, when push out the packing material from the sample column (9), the push-out pin (6) is brought into contact with the packing material while vibrating the push-out pin (6), so that the packing material is pushed out therefrom while being vibrated. Thus, in the present invention, it is possible to reduce adhesion of the packing material into which water is adsorbed, to the inner wall of the sample column (9), and to prevent the packing material, in particular, the alumina fiber from being entangled and stuck around the push-out pin (6) itself. Therefore, in the apparatus for discharging packing material according to the present invention, it is possible to remove the packing material from the sample column (9) smoothly and more certainly, and to supply the packing material to the reaction tube of the analyzer.

Meanwhile, the apparatus for discharging packing material according to the present invention can be applied to not only the above analysis in which the packing material is supplied from the sample column (9) to the analyzer, but also such an analyzing system in which the sample column (9) is directly irradiated with light to conduct analysis therefor and then the packing material after subjected to the analysis is discharged to recover the column. In addition, although in the above embodiment illustrated in the drawings, the analyzer used therein comprises the reaction tube disposed vertically, the apparatus for discharging packing material according to the present invention can also be simply applied to the case where the packing material is discharged from the sample column (9) held horizontally or at any other different angles, by operating the discharge apparatus body (4) so as to align with a center line of the sample column (9).

Incidentally, as a result of conducting the experiment in which one hundred (100) sample columns (9) each filled with activated carbon and alumina fiber as packing materials into which water is adsorbed were prepared and sequentially supplied to the turn table (81) to fall the packing materials from the sample column (9) below the turn table (81) using the apparatus for discharging packing material according to the present invention, it was confirmed that the packing materials were able to be discharged from all of the 100 sample columns (9) smoothly. On the other hand, in the case where the packing materials were discharged from the sample column (9) only by projecting the push-out pin (6) thereinto without operating the motor (7) as a vibration generating means, it was confirmed that in the 8 sample columns (9) among the 100 sample columns, the tip end of the push-out pin (6) was pierced into the packing materials, or the packing materials were entangled and stuck around the tip end of the push-out pin (6), so that the packing materials were drawn back into the sample column (9) with a return motion of the push-out pin (6), which resulted in failure to discharge the packing material from the sample column (9).

The invention claimed is:

1. An apparatus for discharging packing material from a sample column which is adapted to remove the packing material filled in the sample column having a tube shape, comprising:
    a tubular discharge apparatus body which is disposed concentrically to the sample column held in a predetermined position by means of a holding mechanism for the sample column, and which is capable of moving close to and away from the sample column;
    a column positioning hub which is mounted to a tip end of the discharge apparatus body ones the side of the body facing the sample column so as to be movable upward and downward with respect to the column, and which is biased toward the sample column;
    a push-out pin which is inserted into the discharge apparatus body and the column positioning hub to extend substantially along center lines of the discharge apparatus body and the column positioning hub, and which is allowed to relatively project from a tip end of the column positioning hub when the column positioning hub is moved upward with respect to the discharge apparatus body; and
    a vibration generating means for applying vibration to the push-out pin when the push-out pin is allowed to project from the column positioning hub.

2. An apparatus for discharging packing material according to claim 1, wherein the vibration generating means comprises a motor disposed at an upper end portion of the discharge apparatus body, and an eccentric joint which connects an upper end of the push-out pin eccentrically to a rotation axis of the motor.

3. An apparatus for discharging packing material according to claim 1, wherein the column positioning hub is provided at a tip end thereof with a column engaging hole whose diameter is gradually reduced toward the rear end of the column positioning hub.

* * * * *